United States Patent [19]

Marder et al.

[11] E Re. 31,323

[45] Reissued Jul. 26, 1983

[54] PREPARATION OF WATER-INSOLUBLE CARBOXYMETHYL CELLULOSE ABSORBENTS

[75] Inventors: Herman L. Marder, Sommerville; Nathan D. Field, Wyckoff, both of N.J.; Makoto Shinohara, Crystal Lake, Ill.

[73] Assignee: International Playtex, Inc., Stamford, Conn.

[21] Appl. No.: 369,726

[22] Filed: Apr. 19, 1982

Related U.S. Patent Documents

Reissue of:

[64] Patent No.: 4,200,737
Issued: Apr. 29, 1980
Appl. No.: 906,724
Filed: May 17, 1978

[51] Int. Cl.[3] ..... C08B 11/20
[52] U.S. Cl. ..... 536/87; 536/88
[58] Field of Search ..... 536/87, 88; 106/197 C

[56] References Cited

U.S. PATENT DOCUMENTS

| | | | |
|---|---|---|---|
| 1,904,406 | 4/1933 | Callahan | 536/88 |
| 2,639,239 | 5/1953 | Elliott | 106/197 C |
| 2,766,137 | 10/1956 | Ashton et al. | 536/98 |
| 2,772,999 | 12/1956 | Masci et al. | 536/85 |
| 3,379,720 | 4/1968 | Reid | 536/87 |
| 3,379,721 | 4/1968 | Reid | 536/87 |
| 3,391,135 | 7/1968 | Ouno et al. | 536/88 |
| 3,731,686 | 5/1973 | Chatterjee | 536/87 |
| 4,044,766 | 8/1977 | Kaczmarzyk et al. | 536/87 |
| 4,061,859 | 12/1977 | Cheng | 536/88 |
| 4,107,426 | 8/1978 | Gordon | 536/56 |

FOREIGN PATENT DOCUMENTS

| | | | |
|---|---|---|---|
| 1086323 | 10/1967 | United Kingdom | 536/98 |

*Primary Examiner*—Ronald W. Griffin
*Attorney, Agent, or Firm*—Stewart J. Fried

[57] ABSTRACT

A process for the preparation of substantially water-insoluble, particulate sodium carboxymethyl cellulose, suitable for use as an absorbent in tampons and other catamenial devices, or the like. The process involves treating solid, water-soluble sodium carboxymethyl cellulose having a degree of substitution of at least 0.4 with hydrogen chloride gas and heating the carboxymethyl cellulose, either after the hydrogen chloride treatment or concurrently therewith, to produce a cross-linked, insoluble, partially acid form carboxymethyl cellulose suitable for absorbent applications.

7 Claims, No Drawings

PREPARATION OF WATER-INSOLUBLE CARBOXYMETHYL CELLULOSE ABSORBENTS

Matter enclosed in heavy brackets [ ] appears in the original patent but forms no part of this reissue specification; matter printed in italics indicates the additions made by reissue.

BACKGROUND OF THE INVENTION

The present invention relates to an improved method for the preparation of carboxymethyl cellulose (CMC) absorbents and, more particularly, to such a method for the production of water-insoluble, partially acid form CMC's which are so useful.

The use of CMC as an absorbent material in catamenial devices or other absorbent dressings has been known in the literature for a number of years. See, for example, Masci et al U.S. Pat. Nos. 2,764,159 and 2,772,999 granted on Sept. 25 and Dec. 4, 1956, respectively; Ashton et al Pat. No. 2,766,137 granted Oct. 9, 1956; Graham U.S. Pat. No. 3,005,456 granted Oct. 24, 1961 and U.S. Pat. No. 3,055,379 granted Sept. 25, 1962; Burgeni et al U.S. Pat. No. 3,067,745 granted Dec. 11, 1962 and U.S. Pat. No. 3,187,747 granted June 8, 1965; and Lewing U.S. Pat. No. 3,371,666 granted Mar. 5, 1968.

Graham disclosed that only CMC's having a DS value (the number of carboxymethyl groups per anhydroglucose unit in the cellulose chain) less than about 0.35 are useful as absorbents, and described those materials having higher DS values as too soluble for such purpose. It has, however, subsequently been disclosed that CMC's having higher DS values are also suitable for use in absorbent dressings, particularly if insolubilized, e.g., by cross-linking. In this connection reference may be made, for example, to the aforesaid Ashton et al and Masci et al patents; Elliot U.S. Pat. No. 2,639,239 granted May 19, 1953; Dean et al U.S. Pat. No. 3,589,364 granted June 29, 1971; Ells et al U.S. Pat. No. 3,618,607, granted Nov. 9, 1971; Schoggen U.S. Pat. No. 3,678,031, granted July 18, 1972; Chatterjee U.S. Pat. No. 3,731,686, granted May 8, 1973; and Kaczmarzyk et al U.S. Pat. No. 4,044,766, granted Aug. 30, 1977.

The art further teaches that the insolubilized CMC's may be in either the salt form or partially in the acid form, i.e., that a portion, e.g., up to 85%, of the carboxylate groups of the sodium salt are converted to free carboxyl groups. See, for example, the aforesaid Ashton et al, Masci et al, Chatterjee and Kaczmarzyk et al patents, and Reid U.S. Pat. No. 3,379,720, granted Apr. 23, 1968. For purposes of the present invention the proportion of carboxyl groups in the acid form, as a percentage of the carboxylate moieties in the sodium carboxymethyl cellulose salt, is termed the degree of acidification (DA) of the particular CMC salt referenced.

One procedure which has been proposed for preparing water-insoluble CMC's in the partially acid form involves slurrying water-soluble CMC, e.g., sodium CMC, with hydrochloric acid in a water-miscible, organic solvent, e.g., isopropanol, and thereafter insolubilizing the isolated material merely by heat-catalyzed cross-linking. See, for example, the aforesaid Reid patent. Commercial application of such a procedure necessitates the application of solvent recovery techniques to facilitate economic production, and poses the risk of CMC losses in residues from distillation operations which may, for example, be utilized in such techniques. Moreover, the use of solvent recovery operations and the disposal of residues formed therein may additionally pose environmental pollution problems.

A principal object of the present invention is to provide an improved process for the preparation of water-insoluble, acid form CMC materials which may be readily utilized as absorbents for catamenial devices and other absorbent dressings.

It is a further object of the invention to provide such a process which may be commercially employed without substantial materials recovery problems and potential environmental risks as are inherent in the practice of the above-noted prior art procedure.

Other objects and advantages of the process of this invention will be apparent from the following description of preferred embodiments thereof.

SUMMARY OF THE INVENTION

In accordance herewith, a process is provided for the preparation of substantially water-insoluble, particulate CMC suitable for application as an absorbent material. The process involves the direct treatment of a solid water-soluble particulate sodium CMC having a DS value of at least about 0.4 with hydrogen chloride gas, and heating the CMC to convert the same to the desired partially acid form, cross-linked and substantially insolubilized material.

By thus proceeding, water-soluble sodium CMC's having DS values of as low as about 0.4, and generally from about 0.5 to 1.2, may be readily insolubilized. Further, by reacting the CMC in the specific manner indicated, materials are produced having DA values of up to about 80%. Suitable regulation of the DS values of the materials reacted, and the DA values of the partially acid form materials produced, facilitates the formation of insoluble CMC's which exhibit swell ratios of from as little as 5 to as much as 50, and which demonstrate percent extractables (soluble contents) of less than 40 percent.

The insolubilized CMC's thus produced, when incorporated as absorbents in tampons or other catamenial devices, exhibit characteristics comparable to those of insolubilized CMC materials produced by other techniques, e.g., the successive slurry, isolating, drying and curing operations described in the aforesaid Reid patent. Moreover, use of the process hereof does not require extensive solvent recovery operations or entail environmental problems such as posed by such a slurry technique. In addition, this process can be carried out employing lower heat treat temperatures and reaction times than are necessary, for example, to insolubilize CMC in the salt form, e.g., as described in the aforesaid Elliott patent, to produce absorbents of comparable characteristics. The combined HCl gas/heat treatment technique hereof thus appears to effect the desired insolubilization of the initially soluble CMC salt more efficiently, with less concomitant problems, and more rapidly (under the same reaction conditions) than required by prior art processes.

In further contrast with the slurry operations such as have been utilized to prepare partially acid form CMC's in the past, the process of the present invention involves a heterogeneous, solid-vapor contact reaction system. Indeed, the process of the present invention may be carried out with any solid sodium CMC's, independent of the moisture contents thereof—e.g., commercial soluble sodium CMC's having water contents of about 5–10 weight percent (e.g., Hercules, Inc. 7HCF) may be readily converted to insoluble partially acid form CMC's by the process hereof.

The acidification and heat treatment steps of the present process may be carried out either in sequence or concurrently. In addition, the treatment of the soluble CMC with hydrogen chloride gas may be effected either by passing the gas over or through the particulate CMC material.

Whatever particular reaction system is chosen, since the acid-forming reaction is exothermic the external heat load required to effect cross-linking of the soluble CMC is reduced in the present process. The specific time/temperature cycle(s) at which the acidification and heat cross-linking reactions are effected is dependent upon the specific nature of the soluble CMC reactant (i.e., its DS value), the degree of acidification (DA) of the product desired for any particular application, the desired reaction rate, and the concurrent degradation rate of the cellulose substrate (substantial degradation of cellulose occurs at about 230° C.). Generally, the acidification reaction may be carried out at any desired temperature up to about 100° C., the use of ambient temperatures, for example, being particularly convenient. Heat cross-linking, on the other hand, is desirably effected at temperatures in excess of about 100° C., and usually within the range of from about 105° to 200° C., at reaction times varying inversely with the temperature.

Preferred reactants and processing conditions utilized in the practice of the present invention are more fully described in connection with the following preferred embodiments of the invention.

PREFERRED EMBODIMENTS OF THE INVENTION

Any water-soluble, particulate carboxymethyl cellulose salt may be insolubilized in the practice of the present invention. Preferably, the process is carried out employing water-soluble sodium CMC's having DS values of at least 0.4 and most desirably ranging from about 0.5 to 1.2, and the reaction parameters are so regulated as to produce insolubilized, partially acid form materials having DA values of up to 80%, and preferably from about 1–30%. Products thus formed have swell ratios (the degree of swelling with a saline solution as quantitatively defined below) ranging from about 5 to 50 and which may preferably vary from about 5 to 40 (optimally, about 10 to 35). Such products are, moreover, substantially water-insoluble, the percent extractables determined by extraction with a saline solution, as quantitatively defined hereinafter, being less than about 40% and, preferably, less than about 35%.

As noted above, the specific reaction parameters utilized, i.e., the time and temperature conditions, the gas flow rates utilized in the hydrogen chloride acidification step, and the time/temperature cycle employed in the heat cross-linking operation, are dependent upon a number of different variables, including the DS value of the soluble sodium CMC reacted, and the desired characteristics of the insolubilized products (including both the DA desired and the degree of cross-linking and, hence, insolubilization thereof), in addition to the production rate required and, of course, the temperature-dependent degradation rate of the CMC. The particular conditions chosen depend, therefore, both upon the specific characteristics of the absorbent, water-insoluble acid form CMC product desired, and the use of the most efficient reaction parameters for the desired operation.

When the acidification step and heat treatment are conducted sequentially the hydrogen chloride gas is most conveniently reacted with the sodium CMC at initial temperatures less than about 100° C. Employing such conditions, the exothermic acid-forming reaction increases the temperature of the acidified material sometimes to as much as about 100°–125° C.

Heat cross-linking may similarly be carried out over a broad temperature range varying from about ambient temperatures to as much as about 200° C., preferably, from about 105°–200° C. The reaction periods will vary inversely with temperature, and may be further dependent upon the desired reaction rate, the quantity of material to be reacted, etc. Suitable conditions are disclosed, for example, in the aforesaid Reid patent, column 5, lines 56 to 64.

The following examples illustrate a number of particular preferred embodiments of the invention. Unless otherwise indicated therein, all temperatures are specified in degrees Celsius and all parts and percentages are given by weight.

EXAMPLES 1–5

Vapor Phase Acidification of CMC's Having Free Acid Contents Varying from 13 to 79 Percent, and Heat Cross-Linking Thereof at 105° C.

Concentrated hydrochloric acid (36% HCl) was heated to boiling and nitrogen was bubbled therethrough to form a hydrogen chloride gas stream. The gas was dried by bubbling it through concentrated sulfuric acid (98%), and fed, at room temperature into a jar containing dry, granular sodium CMC (Hercules' 7 HCF, having a DS value of 0.7 and a water content of 7.1%). The excess HCl gas passed from the jar and was absorbed in a concentrated $Na_2CO_3$ solution.

In successive runs, CMC's having DA's of 79% (Example 1), 58% (Example 2), 15% (Example 3), 13% (Example 4) and 32% (Example 5) were produced. The percent volatiles (essentially, the water contents) of the respective product samples were also determined, and were 7.6% (Example 1), 8.0% (Example 2), 7.2% (Example 3), 7.1% (Example 4) and 7.7% (Example 5). Upon heating each of these samples for 16 hours in a forced air oven maintained at 105° C. a substantially insoluble material was formed.

EXAMPLES 6–41

Cross-Linking of Acidified CMC's of Examples 3–5 under Varying Heat Treat Cycles Five gram samples of the acidified CMC's prepared as described in Examples 3–5 (prior to heat treatment) were baked in a forced air oven under the time/temperature conditions indicated in Table I below. Control samples of the soluble CMC material (Hercules' 7 HCF) were subjected to similar heat treatments.

The swell ratios and percent extractables exhibited by various of the products thus formed were determined as follows:

Swell Ratios (SR) were calculated by placing 1.00 gram±0.01 gram of the respective samples in a 50 ml. graduated cylinder, filling the cylinder to the 50 ml. mark with a saline solution (0.85%), and shaking the cylinder several times. After 48 hours, the mark to which the sample has swelled was recorded and the swell ratio calculated as:

$$SR = \frac{\text{ml. (sample swelled)}}{\text{bone dry sample weight}}$$

The percent extractables value for each sample was determined by placing 0.4–0.5 grams of the sample in a 100 ml. of saline solution (0.85%) and mixing for 10 minutes, allowing the mixture to settle for 10 minutes, and decanting it into centrifuge tubes. After centrifuging for 10 minutes at 1500–1700 G's, a 25 ml. sample was pipetted into a weighed beaker. 25 ml. of a blank—a 0.85% saline solution—was then pipetted into a weighed beaker. After maintaining both the sample and the blank in a forced air oven overnight at 105° C. the percent extractables was determined by weighing the two materials and calculating the Percent Extractables as follows:

$$\text{Percent Extractables} = (400)\frac{\left[\begin{array}{c}\text{Total sample residue (grams)}\\ -\text{ Blank residue}\end{array}\right]}{\text{Bone Dry sample weight}}$$

The following results were obtained:

TABLE I

VARIED HEAT TREATS OF ACIDIFIED CMC'S

| Example or Control | Material Subjected to Heat Treat | Temperature (°C.) | Time (minutes) | SR | Percent Extractables |
|---|---|---|---|---|---|
| Ex. 6 | Acid CMC of Ex. 5 | 105° | 60 | 34 | — |
| Ex. 7 | Acid CMC of Ex. 5 | " | 120 | 23 | — |
| Ex. 8 | Acid CMC of Ex. 5 (DA = 32%) | " | 180 | 22 | — |
| Ex. 9 | Acid CMC of Ex. 3 | 120° | 60 | 40 | — |
| Ex. 10 | Acid CMC of Ex. 3 | " | 120 | 35 | — |
| Ex. 11 | Acid CMC of Ex. 3 (DA = 15%) | " | 180 | 33 | 23 |
| Ex. 12 | Acid CMC of Ex. 4 | " | 60 | 40 | — |
| Ex. 13 | Acid CMC of Ex. 4 | " | 120 | 36 | — |
| Ex. 14 | Acid CMC of Ex. 4 (DA = 13) | " | 180 | 35 | — |
| Ex. 15 | Acid CMC of Ex. 5 | " | 60 | 20 | — |
| Ex. 16 | Acid CMC of Ex. 5 | " | 120 | 15 | — |
| Ex. 17 | Acid CMC of Ex. 5 (DA = 32%) | " | 180 | 14 | — |
| Control A | Hercules 7 HCF | " | 60 | Essentially soluble, high extractables and some sticky soft gel formed in each instance. | |
| Control B | Hercules 7 HCF | " | 120 | | |
| Control C | Hercules 7 HCF | " | 180 | | |
| Ex. 18 | Acid CMC of Ex. 3 | 138° | 15 | 47 | — |
| Ex. 19 | Acid CMC of Ex. 3 | " | 30 | 33 | 24 |
| Ex. 20 | Acid CMC of Ex. 3 | " | 60 | 28 | — |
| Ex. 21 | Acid CMC of Ex. 3 | " | 120 | 21 | — |
| Ex. 22 | Acid CMC of Ex. 3 (DA = 15%) | " | 180 | 20 | — |
| Ex. 23 | Acid CMC of Ex. 4 | " | 15 | 36 | — |
| Ex. 24 | Acid CMC of Ex. 4 | " | 30 | 37 | — |
| Ex. 25 | Acid CMC of Ex. 4 | " | 60 | 32 | 21 |
| Ex. 26 | Acid CMC of Ex. 4 | " | 120 | 24 | — |
| Ex. 27 | Acid CMC of Ex. 4 (DA = 13%) | " | 180 | 22 | — |
| Ex. 28 | Acid CMC of Ex. 5 | " | 15 | 22 | — |
| Ex. 29 | Acid CMC of Ex. 5 | " | 30 | 16 | — |
| Ex. 30 | Acid CMC of Ex. 5 | " | 60 | 14 | — |
| Ex. 31 | Acid CMC of Ex. 5 | " | 120 | 11 | — |
| Ex. 32 | Acid CMC of Ex. 5 (DA = 32%) | " | 180 | 10 | — |
| Control D | Hercules 7 HCF | " | 60 | Essentially soluble, high extractables and some sticky soft gel formed in each instance. | |
| Control E | Hercules 7 HCF | " | 120 | | |
| Control F | Hercules 7 HCF | " | 180 | | |
| Ex. 33 | Acid CMC of Ex. 3 | 160° | 15 | 48 | — |
| Ex. 34 | Acid CMC of Ex. 3 | " | 30 | 27 | — |
| Ex. 35 | Acid CMC of Ex. 3 (DA = 15%) | " | 60 | 18 | — |
| Ex. 36 | Acid CMC of Ex. 4 | " | 15 | 39 | — |
| Ex. 37 | Acid CMC of Ex. 4 | " | 30 | 31 | — |
| Ex. 38 | Acid CMC of Ex. 4 (DA = 13%) | " | 60 | 16 | — |
| Ex. 39 | Acid CMC of Ex. 5 | " | 15 | 21 | — |
| Ex. 40 | Acid CMC of Ex. 5 | " | 30 | 12 | — |
| Ex. 41 | Acid CMC of Ex. 5 (DA = 32%) | " | 60 | 10 | — |

EXAMPLES 42–54

Acidification with Hydrogen Chloride Charged from Gas Cylinders

More accurate hydrogen chloride gas flow rates were obtained by feeding the gas from a cylinder and metering the same into a nitrogen stream as indicated hereinafter. Initially, the soluble sodium CMC (containing 8.1%) water) was charged to a stirred 3-neck flask. A nitrogen feed stream was passed through the flask and into a caustic absorber. The HCl gas was metered into the nitrogen stream at predetermined rates.

In successive runs acidified products were prepared having DA values of 15.6% (Example 42), 28.2% (Example 43), 10.9% (Example 44), 8.6% (Example 45), 9.3% (Example 46), 2.6% (Example 47), 5.0% (Example 48) and 20% (Example 49).

The acidified products of Examples 47–49 were heat cross-linked with the following results:

TABLE II

HEAT TREATMENT OF ACIDIFIED CMC'S PREPARED BY PROPORTIONED $HCl/N_2$ GAS METERED FLOWS

| Ex. | Material Subjected to Heat Treat | Oven Temperature (°C.) | Time (minutes) | SR | % Extractables |
|---|---|---|---|---|---|
| 50 | Acid CMC of Ex. 47 | 138° | 60 | 39 | 34 |
| 51 | Acid CMC of Ex. 47 (DA = 2.6%) | " | 90 | 30 | 23 |
| 52 | Acid CMC of Ex. 48 | " | 30 | 35 | 42 |
| 53 | Acid CMC of Ex. 48 (DA = 5.0%) | " | 60 | 25 | 21 |
| 54 | Acid CMC of Ex. 49 (DA = 20%) | " | 15 | 36 | 27 |

EXAMPLE 55

Concurrent Acidification and Heat Cross-Linking

The experimental technique described in connection with Examples 42–54 was repeated, the HCl gas being flowed through the granular solid sodium CMC at a temperature of 175°±5° C. for a period of 40 minutes. In one run a cross linked acid form CMC having a free acid content of 4.5% was produced, such product exhibiting the following properties:

SR=28.0

% Extractables=17.8%

% Volatiles<0.1%

The preceding examples are intended as illustrative only of the process of the present invention. It will be understood that various changes may be made in the soluble CMC salts treated, in the time, temperature and other reaction conditions, and in the specific sequence of reaction, without departing from the scope of the invention. Accordingly, other than as defined in the claims appended hereto, this specification should not be interpreted in a limiting sense.

What is claimed is:

1. A process for the preparation of substantially water-insoluble, particulate carboxymethyl cellulose, which comprises treating a solid, water-soluble particulate sodium carboxymethyl cellulose having a degree of substitution of at least 0.4 with hydrogen chloride gas, and heating the carboxymethyl cellulose [at temperatures in excess of 100° C.] to convert the same to a partially acid form, cross-linked and substantially insolubilized material exhibiting a swell ratio of from 5 to 50.

2. The process of claim 1, wherein the sodium carboxymethyl cellulose is heated at temperatures of up to 200° C. to convert the same to a partially acid form having a degree of acidification of as much as 80% and an extractables content of less than 40%.

3. The process of claim 1, wherein the solid sodium carboxymethyl cellulose is initially contacted by the hydrogen chloride gas at temperatures of up to 100° C. and the thus partially acidified particulate material is thereafter heated to temperatures of from 105° to 200° C. to cross-link and insolubilize the same.

4. The process of claim 3, wherein the soluble sodium carboxymethyl cellulose reacted has a degree of substitution of from 0.5 to 1.2 and the insoluble partially acid form carboxymethyl cellulose produced has a degree of acidification of from 1 to 30 percent and exhibits a swell ratio of from 5 to 40 and a percent extractables of less than 35 percent.

5. The process of claim 1, wherein the sodium carboxymethyl cellulose is simultaneously contacted by the hydrogen chloride gas and heated to temperatures of from 105° to 200° C. to produce the cross-linked, insolubilized partially acid form sodium carboxymethyl cellulose product.

6. The process of claim 5, wherein the soluble sodium carboxymethyl cellulose reacted has a degree of substitution of from 0.5 to 1.2 and the insoluble partially acid form carboxymethyl cellulose produced has a degree of acidification of from 1 to 30 percent and exhibits a swell ratio of from 5 to 40 and a percent extractables of less than 35 percent.

7. A process for the preparation of substantially water-insoluble particulate carboxymethyl cellulose, which comprises treating a solid, water-soluble particulate sodium carboxymethyl cellulose having a degree of substitution of from 0.5 to 1.2 with hydrogen chloride gas at a temperature of up to 100° C. to convert the same to a partially acid form carboxymethyl cellulose having a degree of acidification of from 1 to 30 percent; and thereafter heating the carboxymethyl cellulose at temperatures of from 125° to 165° C. to convert the same to a partially acid form, cross-linked and substantially insolubilized material exhibiting a swell ratio of from 5 to 40 and an extractables content of less than 35 percent.

* * * * *